(12) United States Patent
Van Eyk et al.

(10) Patent No.: US 9,678,086 B2
(45) Date of Patent: Jun. 13, 2017

(54) DIAGNOSTIC ASSAY FOR ALZHEIMER'S DISEASE

(71) Applicant: THE JOHNS HOPKINS UNIVERSITY, Baltimore, MD (US)

(72) Inventors: Jennifer Van Eyk, Los Angeles, CA (US); Xiaogian Liu, Baltimore, MD (US); Richard O'Brien, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/427,065

(22) PCT Filed: Sep. 10, 2013

(86) PCT No.: PCT/US2013/058984
§ 371 (c)(1),
(2) Date: Mar. 10, 2015

(87) PCT Pub. No.: WO2014/040042
PCT Pub. Date: Mar. 13, 2014

(65) Prior Publication Data
US 2015/0212098 A1    Jul. 30, 2015

Related U.S. Application Data

(60) Provisional application No. 61/699,105, filed on Sep. 10, 2012.

(51) Int. Cl.
    G01N 33/53   (2006.01)
    G01N 24/00   (2006.01)
    G01N 33/68   (2006.01)

(52) U.S. Cl.
    CPC ..... *G01N 33/6896* (2013.01); *G01N 33/6848* (2013.01); *G01N 2333/4703* (2013.01); *G01N 2333/775* (2013.01); *G01N 2560/00* (2013.01); *G01N 2800/2821* (2013.01)

(58) Field of Classification Search
    None
    See application file for complete search history.

(56) References Cited

U.S. PATENT DOCUMENTS

| 8,232,066 B2 | 7/2012 | Van Eyk et al. |
| 8,771,969 B2 | 7/2014 | Van Eyk et al. |
| 2005/0244890 A1 | 11/2005 | Davies et al. |
| 2009/0142766 A1 | 6/2009 | Holtzman et al. |
| 2010/0021938 A1 | 1/2010 | Boutaud |
| 2010/0221759 A1 | 9/2010 | Multhaup et al. |
| 2011/0165146 A1 | 7/2011 | Westbrook et al. |

FOREIGN PATENT DOCUMENTS

WO    2010065878 A1    6/2010

OTHER PUBLICATIONS

O'Brien, R., et al "Amyloid Precursor Protein Processing and Alzheimer's Disease," Annu. Rev. Neurosci. 2011. 34:185-204.
Lame, M., et al. "Quantitation of amyloid β peptides Aβ(1-38), Aβ(1-40), and Aβ(1-42) in human cerebrospinal fluid by ultra-performance liquid chromatography-tandem mass spectrometry." Anal Biochem. Dec. 15, 2011;419(2):133-139.
Oe, T. et al. "Quantitative analysis of amyloid β peptides in cerebrospinal fluid of Alzheimer's disease patients by immunoaffinity purification and stable isotope dilution liquid chromatography/negative electrospray ionization tandem mass spectrometry." Rapid Commun Mass Spectrom. 2006;20(24):3723-3735.
Goda, R., et al. "Evaluation of peptide adsorption-controlled liquid chromatography-tandem mass spectrometric (PAC-LC-MS/MS) method for simple and simultaneous quantitation of amyloid β 1-38, 1-40, 1-42 and 1-43 peptides in dog cerebrospinal fluid." J Chromatogr B Analyt Technol Biomed Life Sci. May 1, 2012;895-896:137-145.

*Primary Examiner* — Olga N Chernyshev
(74) *Attorney, Agent, or Firm* — Johns Hopkins Technology Transfer

(57) ABSTRACT

The present invention relates to the field of Alzheimer's disease (AD). More specifically, the present invention provides methods and compositions useful in diagnosing and assessing AD. In another embodiment, a method for diagnosing Alzheimer's Disease (AD) in a patient comprises the steps of (a) obtaining CSF sample from the patient; (b) adding to the sample isotopically labeled peptides identical to a portion of one or more biomarker proteins, wherein the one or more biomarker proteins comprise total APP, APP isoform 751, APP isoform 770, amyloid beta 40 peptide, APOE, and Clusterin; and (c) measuring the one or more biomarker proteins in the sample using mass spectrometry, wherein the level of one or more biomarker proteins compared to a control correlates with AD in the patient.

3 Claims, 20 Drawing Sheets

WYFDVTEGK  SEQ ID NO:3

FIG. 5E

WYFDVTEGK  SEQ ID NO:3

FIG. 5F

GAIIGLMVGGVV SEQ ID NO:5

FIG. 5I

GAIIGLMVGGVV SEQ ID NO:5

DIAGNOSTIC ASSAY FOR ALZHEIMER'S DISEASE

CROSS-REFERENCE TO RELATED APPLICATIONS

This application is a 35 U.S.C. §371 U.S. national entry of International Application PCT/US2013/058984, having an international filing date of Sep. 10, 2013, which claims the benefit of U.S. Provisional Application No. 61/699,105, filed Sep. 10, 2012, the content of each of the aforementioned applications is herein incorporated by reference in their entirety.

FIELD OF THE INVENTION

The present invention relates to the field of Alzheimer's disease (AD). More specifically, the present invention provides methods and compositions useful in diagnosing and assessing AD.

INCORPORATION-BY-REFERENCE OF MATERIAL SUBMITTED ELECTRONICALLY

This application contains a sequence listing. It has been submitted electronically via EFS-Web as an ASCII text file entitled "P12148-02_Sequence_Listing.txt." The sequence listing is 2,023 bytes in size, and was created on Sep. 10, 2013. It is hereby incorporated by reference in its entirety.

BACKGROUND OF THE INVENTION

Alzheimer's disease is the principal cause of dementia and the most common neurodegenerative disease. This disease, progressive in nature, is characterized by memory loss and degradation of language skills, orientation and judgment. The nature of the symptoms, which are often confused with the physiological troubles of old age, severity and the age at which they appear vary from individual to individual. This contributes to the difficulty in establishing a diagnosis during the early stages of the disease.

Currently, there is no robust and specific signature for Alzheimer's disease that makes it possible to diagnose this pathology, most notably the various stages of the progression of the disease. The availability of an effective diagnostic test, in particular an early test, would enable patients to be cared for at the onset of the disease and thus to benefit from more effective and suitable treatments under optimal conditions.

SUMMARY OF THE INVENTION

The present invention is based, at least in part, on the discovery that the measurement of one or more biomarker proteins can be used to diagnose AD. More specifically, the measurement of one of more proteins including amyloid precursor protein, peptides thereof (including amyloid beta peptide), apolipoprotein E (APOE) and Clusterin can be used to diagnose AD. Indeed, the present inventors have developed an integrated mass spectrometry assay to measure such proteins/peptides.

Accordingly, in one aspect, the present invention provides methods and compositions useful for diagnosing AD in a patient. In one embodiment, a method for diagnosing Alzheimer's Disease (AD) in a patient comprises the steps of (a) measuring one or more biomarker proteins using mass spectrometry on a cerebrospinal fluid sample taken from the patient; and (b) correlating the measured proteins to AD in the patient based on the level of the one or more biomarker proteins or a ratio of between two or more fragments thereof. In certain embodiments, the one or more biomarker proteins comprise total amyloid precursor protein (APP), APP isoform 751, APP isoform 770, amyloid beta 40 peptide, apolipoprotein E (APOE), and Clusterin. In particular embodiments, the mass spectrometry is selected reaction monitoring (SRM) mass spectrometry. In a specific embodiment, the measuring step is accomplished using isotopically labeled peptides of the one or more biomarker proteins added to the CSF sample to aid in quantitation. In such embodiment, the one or more biomarker proteins comprise total APP, APP isoform 751, APP isoform 770, amyloid beta 40 peptide, APOE, and Clusterin. In some embodiments, the isotopically labeled peptides comprise one or more of SEQ ID NOS: 1-11.

In another embodiment, a method for diagnosing Alzheimer's Disease (AD) in a patient comprises the steps of (a) obtaining CSF sample from the patient; (b) adding to the sample isotopically labeled peptides identical to a portion of one or more biomarker proteins, wherein the one or more biomarker proteins comprise total APP, APP isoform 751, APP isoform 770, amyloid beta 40 peptide, APOE, and Clusterin; and (c) measuring the one or more biomarker proteins in the sample using mass spectrometry, wherein the level of one or more biomarker proteins compared to a control correlates with AD in the patient. In particular embodiments, the isotopically labeled peptides comprise one or more of SEQ ID NOS: 1-11. In certain embodiments, the mass spectrometry is SRM mass spectrometry.

The present invention also provides a method for diagnosing Alzheimer's Disease (AD) in a patient comprising the steps of (a) obtaining CSF sample from the patient; (b) adding to the sample isotopically labeled peptides identical to a portion of one or more biomarker proteins, wherein the one or more biomarker proteins comprise total APP, APP isoform 751, APP isoform 770, amyloid beta 40 peptide, APOE, and Clusterin; and (c) measuring the one or more biomarker proteins in the sample using mass spectrometry, wherein the ratio of two or more peptide fragments of one or more of the biomarker proteins correlates with AD in the patient. In one embodiment, the isotopically labeled peptides comprise one or more of SEQ ID NOS: 1-11. In certain embodiments, the mass spectrometry is SRM mass spectrometry. In other embodiments, the isotopically labeled peptides identical to a portion of APP comprise SEQ ID NOS:1-3. In a further embodiment, the isotopically labeled peptides identical to a portion of amyloid beta 40 peptide comprise SEQ ID NOS:4-5. In yet another embodiment, the isotopically labeled peptides identical to a portion of APOE comprise SEQ ID NOS:6-8. In a specific embodiment, the isotopically labeled peptides identical to a portion of Clusterin comprise SEQ ID NOS:9-11.

BRIEF DESCRIPTION OF THE FIGURES

FIGS. 5A-5J. Amyloid precursor protein (APP) and Amyloid beta (Aβ) concentrations in Cerebrospinal fluid samples. FIG. 5A Peptide THPHFVIPYR (SEQ ID NO:1)

concentration measured in nine pooled CSF samples. FIG. 5B Peptide THPHFVIPYR (SEQ ID NO:1) concentration measured in Non-dementia and Dementia individual CSF samples. FIG. 5C Peptide EWEEAER (SEQ ID NO:2) concentration measured in nine pooled CSF samples. FIG. 5D Peptide EWEEAER (SEQ ID NO:2) concentration measured in Non-dementia and Dementia individual CSF samples. FIG. 5E Peptide WYFDVTEGK (SEQ ID NO:3) concentration measured in nine pooled CSF samples. FIG. 5F Peptide WYFDVTEGK (SEQ ID NO:3) concentration measured in Non-dementia and Dementia individual CSF samples. FIG. 5G Peptide LVFFAEDVGSNK (SEQ ID NO:4) concentration measured in nine pooled CSF samples. FIG. 5H Peptide LVFFAEDVGSNK (SEQ ID NO:4) concentration measured in Non-dementia and Dementia individual CSF samples. FIG. 5I Peptide GAIIGLMVGGVV (SEQ ID NO:5) concentration measured in nine pooled CSF samples. FIG. 5J Peptide LVFFAEDVGSNK (SEQ ID NO:5) concentration measured in Non-dementia and Dementia individual CSF samples.

DETAILED DESCRIPTION OF THE INVENTION

Figure 1:
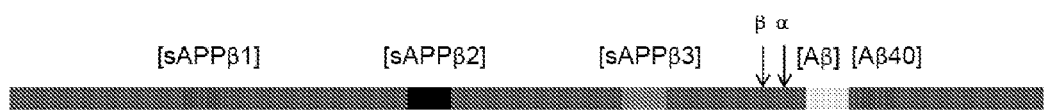
FIG. 1. Schematic of APP protein and the locations of five peptides.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

The following definitions are used throughout this specification. Other definitions are embedded within the specification for ease of reference.

As used herein, "comparing" refers to making an assessment of how the proportion, level or cellular localization of one or biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample.

As used herein, "indicates" or "correlates" (or "indication" or "correlation," depending on the context) in reference to a parameter, e.g., a modulated proportion, level, or cellular localization in the cell from a patient, may mean that the patient has AD. In specific embodiments, the parameter may comprise the presence, absence and/or particular amounts of one or more biomarkers of the present invention. A particular set or pattern of one or more biomarkers (including the presence, absence, and/or particular amounts) may indicate that a patient has AD (or correlated to a patient having AD), in particular, AD. In other embodiments, a particular set or pattern of one or more biomarkers (including the presence, absence, and/or particular amounts) may be correlated to a patient having AD. In yet other embodiments, a particular set or pattern of one or more biomarkers (including the presence, absence, and/or particular amounts) may be correlated to a patient being unaffected. In certain embodiments, "correlating" or "normalization" as used according to the present invention may be by any method of relating levels of expression or localization of markers to a standard valuable for the: assessment of the diagnosis, prediction of AD or AD progression, assessment of efficacy of clinical treatment, identification of a tumor that may respond to a treatment, selection of a patient for a particular treatment, monitoring of the progress of treatment, and in the context of a screening assay, for the identification of an anti-AD therapeutic.

The terms "individual," "subject" or "patient" are used interchangeably herein, and refer to a mammal, particularly, a human. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The term "measuring" means methods which include detecting the presence or absence of a biomarker(s) in a sample, quantifying the amount of biomarker(s) in the sample, and/or qualifying the type of biomarker(s). Measuring can be accomplished by methods known in the art and those further described herein including, but not limited to, polymerase chain reaction. The term "measuring" is used interchangeably throughout with the term "detecting" and "performing an assay."

Various methodologies of the instant invention include a step that involves comparing a value, level, feature, characteristic, property, etc. to a "suitable control," referred to interchangeably herein as an "appropriate control," a "control sample" or a "reference." A "suitable control," "appropriate control," a "control sample" or a "reference" is any control or standard familiar to one of ordinary skill in the art useful for comparison purposes. In one embodiment, a "suitable control" or "appropriate control" is a value, level, feature, characteristic, property, etc. determined in a cell, organ, or patient, e.g., a control or normal cell, organ, or patient, exhibiting, for example, normal traits. For example, the biomarkers of the present invention may be assayed for their presence in a sample from an unaffected individual (UI) or a normal control individual (NC) (both terms are used interchangeably herein). In another embodiment, a "suitable control" or "appropriate control" is a value, level, feature, characteristic, property, etc. determined prior to performing an AD therapy on a patient. In yet another embodiment, a transcription rate, mRNA level, translation rate, protein level, biological activity, cellular characteristic or property, genotype, phenotype, etc. can be determined prior to, during, or after administering an AD therapy into a cell, organ, or patient. In a further embodiment, a "suitable control" or "appropriate control" is a predefined value, level, feature, characteristic, property, etc.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of AD. Moreover, a sample obtained from a patient can be divided and only a portion may be used for diagnosis. Further, the sample, or a portion thereof, can be stored under conditions to maintain sample for later analysis. The definition specifically encompasses cerebrospinal fluid, blood and other liquid samples of biological origin (including, but not limited to, peripheral blood, serum, plasma, saliva, stool and synovial fluid), solid tissue samples such as a biopsy specimen or tissue cultures or cells derived therefrom and the progeny thereof. In certain embodiments, a sample comprises cerebrospinal fluid. In a specific embodiment, a sample comprises a blood sample. In another embodiment, a sample comprises a plasma sample. In yet another embodiment, a serum sample is used.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

II. Detection of AD Biomarkers by Mass Spectrometry

In one aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the present invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic coelution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application the terms SRM and MRM or also SRM/MRM can be used interchangeably, since they both refer to the same mass spectrometer operating principle. As a matter of clarity, the term SRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique comprises surface enhanced laser desorption and ionization or "SELDI," as described, for example, in U.S. Pat. Nos. 6,225,047 and 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

III. Biomarkers for AD

In one aspect, the present invention provides a panel of peptides as biomarkers for AD. In particular embodiments, biomarkers that are present at elevated levels in patients with AD are used as biomarkers. In other embodiments, biomarkers that are present at reduced levels in the patients with AD are used as biomarkers. In some embodiments, more than one biomarker can be used as biomarkers. In such cases, the biomarker may all have elevated levels, all have reduced levels, or a mixture of biomarker with elevated and reduced levels may be used. In particular embodiments, the biomarker can be detected in a patient sample which includes, but is not limited to, cerebrospinal fluid (CSF).

The terms "reduced levels" or "elevated levels" refer to the amount of a biomarker in a sample from a patient compared to the amount of the biomarker from a suitable control. For example, a biomarker present in the CSF of an AD patient may be determined to be present at lower amounts than in CSF from a subject who does not have AD. For certain biomarker, elevated levels in a patient CSF sample correlate or indicate presence of or prognosis for AD. Other biomarkers are present in reduced levels in patients with AD.

In particular embodiments, the level of the biomarker marker will be compared to a suitable control to determine whether the level is reduced or elevated. The control may be an external control, such as a biomarker in a CSF sample from a patient known to be free of AD or a reference level. In other embodiments, the external control may be a biomarker from a non-CSF sample like a tissue sample. An internal control may be a biomarker from the same CSF sample being tested. The identity of a biomarker control may be the same as or different from the patient CSF biomarker being measured.

The terms "characterizing" and "identifying" includes making diagnostic or prognostic determinations or predictions of disease. In some instances, "characterizing" and "identifying" include identifying whether a subject has AD. The terms "characterizing" and "identifying" further includes distinguishing patients with AD from patients having other diseases. In other circumstances, "characterizing" includes determining the stage or aggressiveness of a disease state such as AD, determining an appropriate treatment method for AD, or assessing the effectiveness of a treatment for AD.

The methods of the present invention can be used to characterize a patient with at least about 80%, at least about 85%, at least about 90%, at least about 91%, at least about 92%, at least about 93%, at least about 94%, at least about 95%, at least about 96%, at least about 97%, at least about 98%, or at least about 99% sensitivity. The degree of sensitivity indicates the percentage of patients with a disease who are positively characterized as having the disease. The methods described herein can also be used to characterize a patient with at least about 80%, at least about 85%, at least about 90%, at least about 91%, at least about 92%, at least about 93%, at least about 94%, at least about 95%, at least about 96%, at least about 97%, at least about 98%, or at least about 99% specificity (e.g., the percentage of non-diseased patients who are correctly characterized). The assay parameters can be adjusted to optimize for both sensitivity and specificity.

A. Biomarker Panels

The biomarkers of the present invention can be used in diagnostic tests to assess, characterize, determine, and/or qualify (used interchangeably herein) AD status in a subject. The phrase "AD status" includes any distinguishable manifestation of the disease, including non-disease. For example, AD status includes, without limitation, the presence or absence of AD (e.g., distinguishing between unaffected individuals (UI) and AD in a subject), the risk of developing AD, the stage of the AD, the progress of AD (e.g., progress of AD or regression of AD over time) and the effectiveness or response to treatment of AD (e.g., clinical follow up and surveillance of AD after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different AD statuses of at least about $p<0.05$, at least about $p<10^{-2}$, at least about $p<10^{-3}$, at least about $p<10^{-4}$ or at least about $p<10^{-5}$. Diagnostic tests that use these biomarkers may show a sensitivity and specificity of at least about 70%, at least about 75%, at least about 80%, at least about 85%, at least about 90%, at least about 95%, at least about 98% and about 100%.

The biomarkers are differentially present in UI (or normal control individuals (NC)), and, therefore, are useful in aiding in the determination of AD status. In certain embodiments, the biomarkers are measured in a patient sample using the methods described herein. The measurement(s) may then be compared with a relevant diagnostic amount(s) or cut-off(s) that distinguish a positive AD status from a negative AD status. The diagnostic amount(s) represents a measured amount of a biomarker(s) above which or below which a subject is classified as having a particular AD status. For example, if the biomarker(s) is/are up-regulated compared to normal during AD (e.g., elevated levels), then a measured amount(s) above the diagnostic cutoff(s) provides a diagnosis of AD. Alternatively, if the biomarker(s) is/are down-regulated during AD (e.g., reduced levels), then a measured amount(s) below the diagnostic cutoff(s) provides a diagnosis of AD. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of the biomarker(s) in a statistically significant number of samples from subjects with the different AD statuses, and drawing the cut-off to suit the desired levels of specificity and sensitivity.

Indeed, as the skilled artisan will appreciate there are many ways to use the measurements of two or more biomarkers in order to improve the diagnostic question under investigation. In a quite simple, but nonetheless often effective approach, a positive result is assumed if a sample is positive for at least one of the markers investigated.

Frequently, however, the combination of biomarkers is evaluated. In particular embodiments, the values measured for biomarkers of a biomarker panel are mathematically combined and the combined value is correlated to the underlying diagnostic question. MicroRNA biomarker values may be combined by any appropriate state of the art mathematical method. Well-known mathematical methods for correlating a marker combination to a disease employ methods like discriminant analysis (DA) (e.g., linear-, quadratic-, regularized-DA), Kernel Methods (e.g., SVM), Non-parametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will recognize an appropriate method to evaluate a biomarker combination of the present invention. In certain embodiments, the method used in correlating biomarker combination of the present invention is selected from DA (e.g., Linear-, Quadratic- and Regularized DA), Kernel Methods (e.g., SVM), Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression). Details relating to these statistical methods are found in the following references: Pepe, M. S., The Statistical Evaluation of Medical Tests for Classification and Prediction, Oxford Statistical Science Series, 28 (2003); Ruczinski et al., 12 J. OF COMPUTATIONAL AND GRAPHICAL STATISTICS 475-511 (2003); Breiman, L., 45 MACHINE LEARNING 5-32 (2001); Duda, R. O., Hart, P. E., Stork, D. G., Pattern Classification, Wiley Interscience, 2nd Edition (2001); Hastie, Trevor, Tibshirani, Robert, and Friedman, Jerome, The Elements of Statistical Learning, Springer Series in Statistics (2001); Friedman, J. H., 84 J. OF THE AMERICAN STATISTICAL ASSOCIATION 165-75 (1989); Breiman, L., Friedman, J. H., Olshen, R. A., and Stone, C. J. Classification and regression trees, California: Wadsworth (1984).

B. Determining Risk of Developing AD

In a specific embodiment, the present invention provides methods for determining the risk of developing AD in a subject. Biomarker amounts or patterns are characteristic of various risk states, e.g., high, medium or low. The risk of developing AD is determined by measuring the relevant biomarkers and then either submitting them to a classification algorithm or comparing them with a reference amount and/or pattern of biomarkers that is associated with the particular risk level.

C. Determining Stage of AD

In another embodiment, the present invention provides methods for determining the stage of AD in a subject. Each stage of the AD has a characteristic amount of a biomarker or relative amounts of a set of biomarkers (a pattern). The stage of AD is determined by measuring the relevant biomarkers and then either submitting them to a classification algorithm or comparing them with a reference amount and/or pattern of biomarkers that is associated with the particular stage.

D. Determining Course (Progression/Regression) of AD

In one embodiment, the present invention provides methods for determining the course of AD in a subject. AD course refers to changes in AD status over time, including AD progression (worsening) and AD regression (improvement). Over time, the amounts or relative amounts (e.g., the pattern) of the biomarkers change. For example, biomarker "X" is increased with AD, while biomarker "Y" may be decreased in AD. Therefore, the trend of these biomarkers, either increased or decreased over time toward AD or non-AD indicates the course of the disease. Accordingly, this method involves measuring one or more biomarkers in a subject at least two different time points, e.g., a first time and a second time, and comparing the change in amounts, if any. The course of AD is determined based on these comparisons.

E. Subject Management

In certain embodiments of the methods of qualifying or determining AD status, the methods further comprise managing subject treatment based on the status. Such management includes the actions of the physician or clinician subsequent to determining AD status. For example, if a physician makes a diagnosis of AD, then a certain regime of monitoring might follow. A diagnosis of AD may also require a certain AD therapy regimen. Alternatively, a diagnosis of non-AD might be followed with further testing to determine a specific disease that the patient might be suffering from. Also, further tests may be called for if the diagnostic test gives an inconclusive result on AD status.

F. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of one or more of the biomarkers of the present invention may change toward a non-AD profile. Therefore, one can follow the course of the amounts of one or more biomarkers in the subject during the course of treatment. Accordingly, this method involves measuring one or more biomarkers in a subject receiving drug therapy, and correlating the amounts of the biomarkers with the AD status of the subject. One embodiment of this method involves determining the levels of one or more biomarkers at least two different time points during a course of drug therapy, e.g., a first time and a second time, and comparing the change in amounts of the biomarkers, if any. For example, the one or more biomarkers can be measured before and after drug administration or at two different time points during drug administration. The effect of therapy is determined based on these comparisons. If a treatment is effective, then one or more biomarkers will trend toward normal, while if treatment is ineffective, the one or more biomarkers will trend toward AD indications.

G. Generation of Classification Algorithms for Qualifying AD Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain et al., "Statistical Pattern Recognition: A Review", 22(1) IEEE TRANSACTIONS ON PATTERN ANALYSIS AND MACHINE INTELLIGENCE (2000).

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART-classification and regression trees), artificial neural networks such as back propagation networks, discriminant analyses (e.g., Bayesian classifier or Fischer analysis), logistic classifiers, and support vector classifiers (support vector machines). Another supervised classification method is a recursive partitioning process. Recursive partitioning processes use recursive partitioning trees to classify data derived from unknown samples. See U.S. Patent Application Publication No. 2002/0138208.

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm. Learning algorithms asserted for use in classifying biological information are described, for example, in WO 01/31580, U.S. Patent Applications Publication No. 2003/0055615, No. 2003/0004402, and No. 2002/0193950.

The classification models can be formed on and used on any suitable digital computer. Suitable digital computers include micro, mini, or large computers using any standard or specialized operating system, such as a Unix, Windows® or Linux™ based operating system. The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, and for finding new biomarkers. The classification algorithms, in turn, form the base for diagnostic tests by providing diagnostic values (e.g., cut-off points) for biomarkers used singly or in combination.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Amyloid Precursor Protein (APP), Amyloid Beta Peptide, APOE and Clusterin Protein Study by Selected Reaction Monitoring (SRM) Mass Spectrometry in Alzheimer's Disease Amyloid precursor protein (APP) is a single-pass transmembrane protein with a long N-terminal extracellular domain and a short cytoplasmic domain found in the brain. It has three major isoforms, APP770, 751, 695. Sequential cleavages of APP protein by proteases β-secretase and γ-secretase generate soluble APPβ protein and neurotoxic amyloid β (Aβ) peptides, Aβ-40 and Aβ-42. Plaque, consisting of Aβ peptides, located in brain is the pathological evidence of Alzheimer's Disease (AD). Although APP protein plays an important role in AD formation, the concentration of the various forms of APP that occur in brain is not clear, nor is it known what forms are present in cerebrospinal fluid (CSF). Our study is to measure APP cleavage products, this will help to unveil the mechanism of AD. The schematic of APP protein is shown in FIG. 1.

Materials and Methods

Chemicals and reagents. Amyloid β-40 peptide was purchased from Bachem (Torrance, Calif.). sAPPβ recombinant protein was purchased from Covance (Dedham, Mass.). Synthetic isotopically labeled peptides were purchased from New England Peptide (Gardner, Mass.). Artificial CSF perfusion fluid was purchased from Harvard Apparatus (Holliston, Mass.). Water for sample preparation was obtained from a Milli-Q lab water system (Millipore, Billerica, Mass.). Acetonitrile, methanol, and formic acid were purchased from Fisher Scientific (Fair Lawn, N.J.). All other chemicals and reagents were purchased from Sigma (St. Louis, Mo.). Oasis HLB 96-well plate was purchased from Waters (Milford, Mass.).

Instruments. 5500 QTRAP triple quadrupole mass spectrometer (ABSciex, Farmingham, Mass.) coupled to dual Prominence UFLCXR HPLC (Shimadzu Scientific Instruments, Columbia, Md.). HPLC column: Xbridge BEH30 C18 (2.1 mm×100 mm, 3.5 μm, Waters, Milford, Mass.).

Software. MRMPilot™, 2.1 (ABSciex, Farmingham, Mass.) Analyst, 1.5.2 (ABSciex, Farmingham, Mass.); MultiQuant, 2.1 (ABSciex, Farmingham, Mass.)

MRM Assay Work Flow

Figure 2:
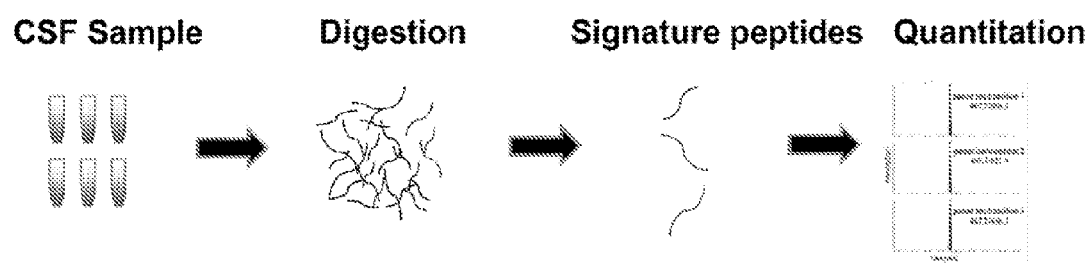
FIG. 2. Schematic of assay work flow.

CSF samples were collected from Johns Hopkins hospital. Samples were digested to peptides by enzyme trypsin, under conditions to ensure complete digestion. Signature peptides were selected from each targeted fragment. MRM transitions for each peptide were selected by mass spectrometer. Proteins were quantified by optimized MRM transitions of signature peptide. The work flow is shown in FIG. 2.

Experimental Protocol

In this study, we have three different cerebrospinal fluid (CSF) sample types: (1) Nine pooled CSF samples, their IDs are listed in Table 1; (2) Thirteen individual CSF samples, six are non-dementia, seven are dementia, their IDs are listed in Table 2: and (3) Sixty gender and age matched CSF samples. They were divided into six groups, including YNM, ONM, AMD, YNF, ONF, and AFD. 100 μl of CFS was processed. Beta Gal protein was spiked as an internal standard.

TABLE 1

Pooled Cerebrospinal fluid (CSF) sample ID.

| Pooled CSF | ID | Gender | Age |
|---|---|---|---|
| YNM | Young Normal Male | Male | 20-39 |
| ONM | Old Normal Male | Male | 71-84 |
| AMD | Adult Male Demented | Male | 61-90 |
| YNF | Young Normal Female | Female | 19-37 |
| ONF | Old Normal Female | Female | 70-84 |
| AFD | Adult Female Demented | Female | 67-90 |
| FTD | Frontotemporal Dementia | Mixed | 64-87 |
| NPH | Normal Pressure Hydrocephalus | Mixed | 62-84 |
| PTC | Pseudotumor Cerebri | Female | 21-50 |

TABLE 2

Individual CSF sample ID

| Non-dementia | | | Dementia | | |
|---|---|---|---|---|---|
| ID | Gender | Age | ID | Gender | Age |
| ONM | M | 83 | AMD1 | M | 75 |
| ONF1 | F | 40 | AMD2 | M | 85 |
| ONF2 | F | 62 | AMD3 | M | 77 |
| PTC1 | F | 32 | AMD4 | M | 77 |
| PTC2 | F | 38 | AFD1 | F | 76 |
| PTC3 | F | 29 | AFD2 | F | 85 |
| | | | AFD3 | F | 68 |

Recombinant protein sAPPβ and synthetic amyloid β-40 peptide were added to 100 μl artificial CSF to prepare calibration standards. Protein, peptide, and samples were denatured by RapiGest; reduced by 20 mM DTT at 55° C. for 50 minutes; alkylated by 50 mM IAA at room temperature in the dark, and then digested by trypsin at 37° C. overnight.

The isotopic labeled peptides were added as internal standards. Samples were desalted by Oasis HLB 96-well plate prior to analysis by LC-MS/MS.

Results

Figure 3:
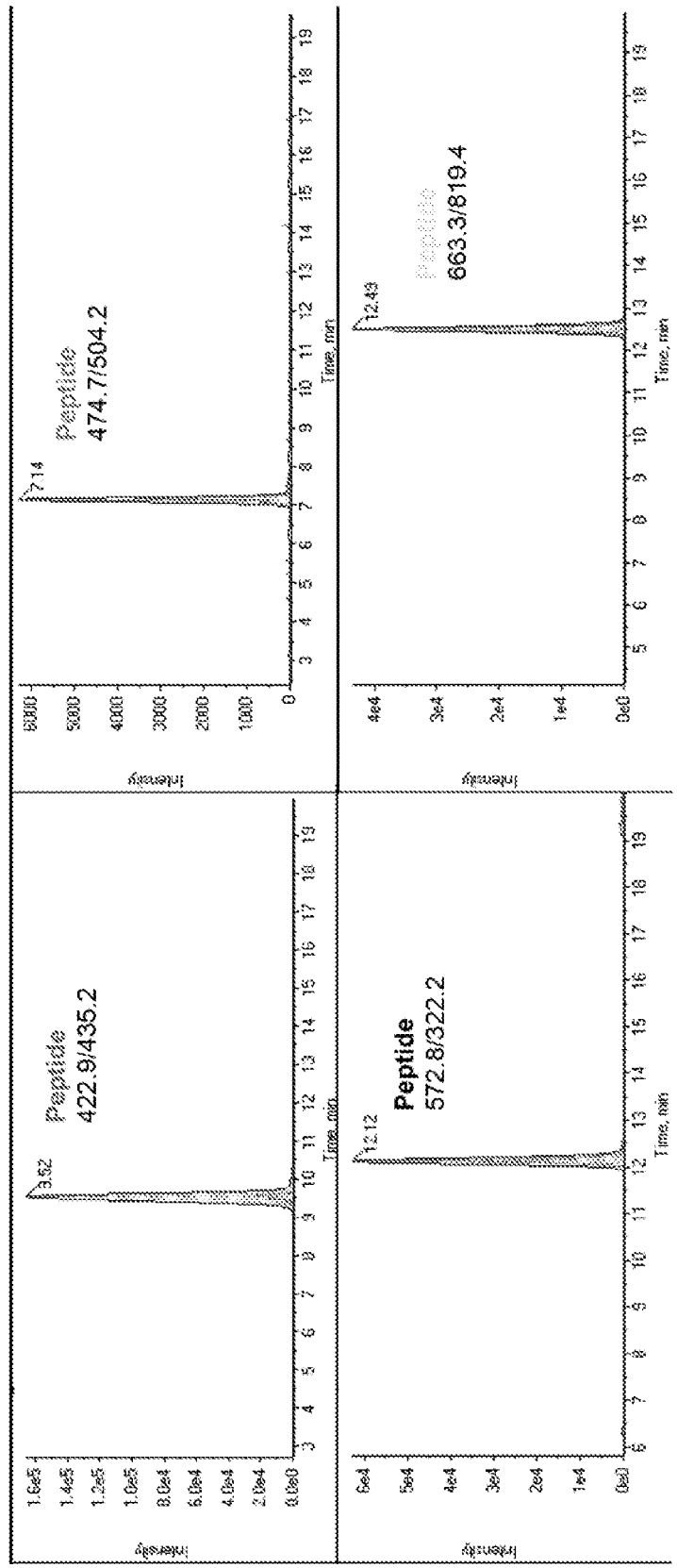
FIG. 3. Chromatograms of signature peptides and isotopic labeled peptides.
Figures 4A, 4B:
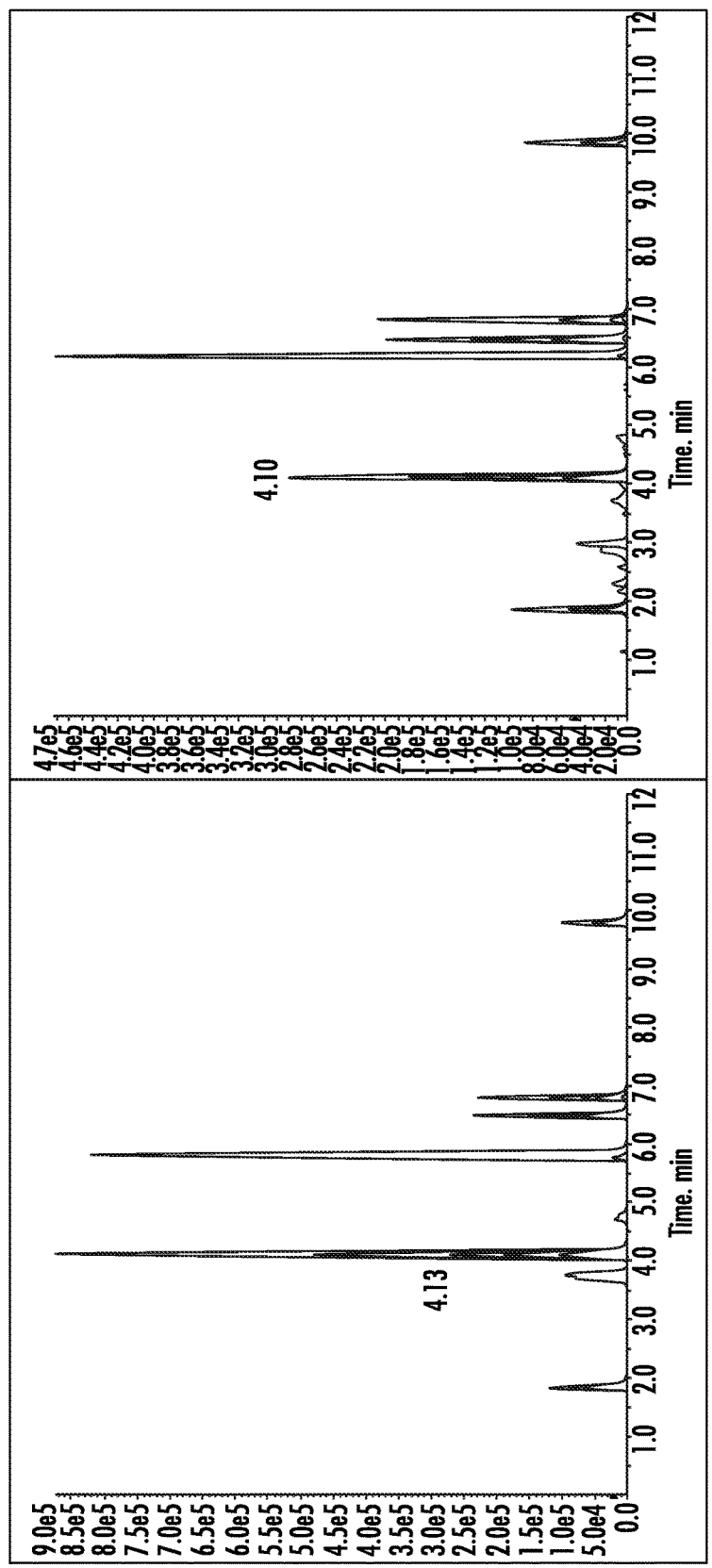
FIG. 4A. Chromatogram of heavy labeled peptides.
FIG. 4B. Chromatogram of peptides from dementia CSF sample.

Representative chromatograms of signature peptides and their isotopic labeled peptides are shown in FIG. 3. Calibration curves were established based on the ratio of the peak area of light and heavy peptide versus concentration. Calibration range was from 1.0-100.0 fmol/μl. LLOQ was 1.0 fmol/μl.

Figure 5A:
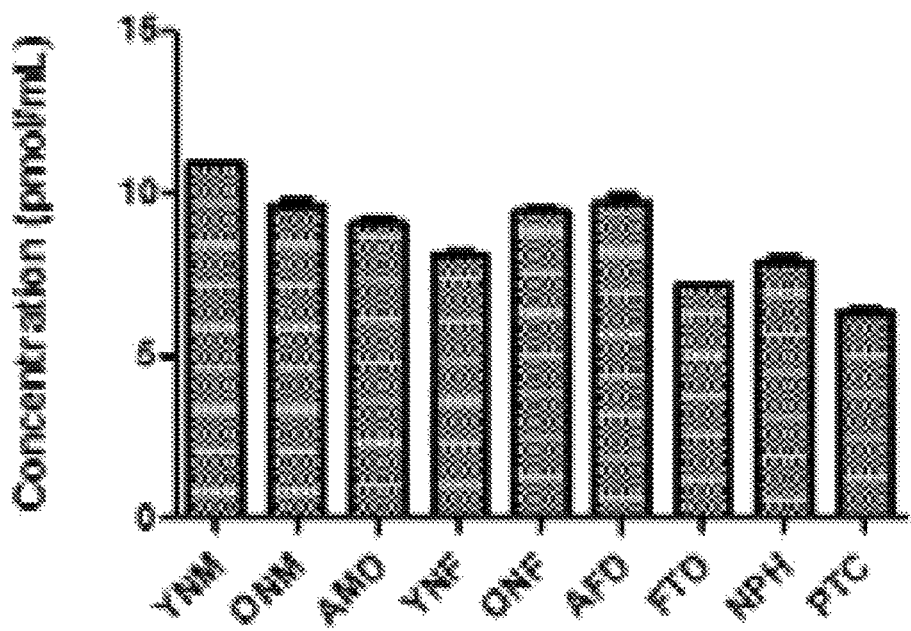
Figure 5B:
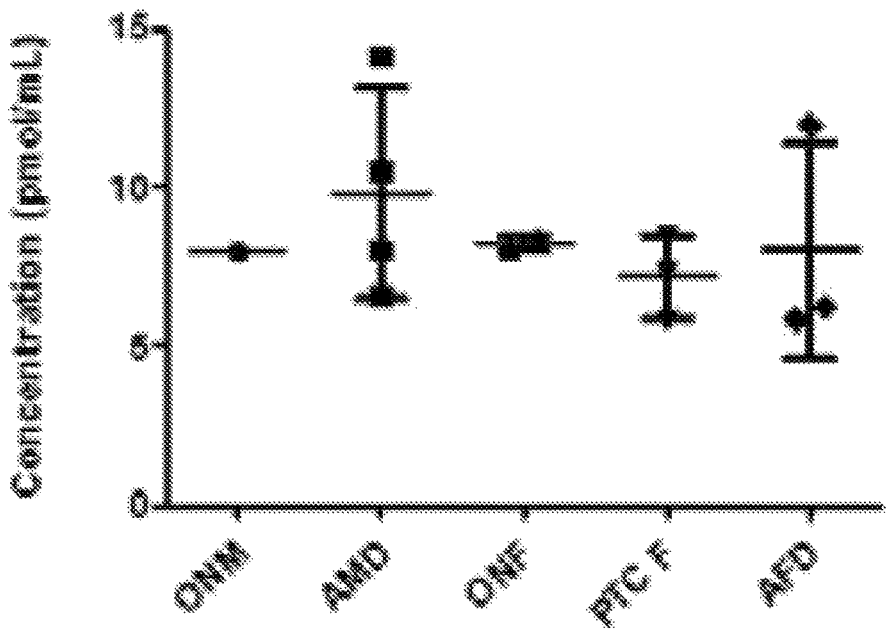
Figure 5C:
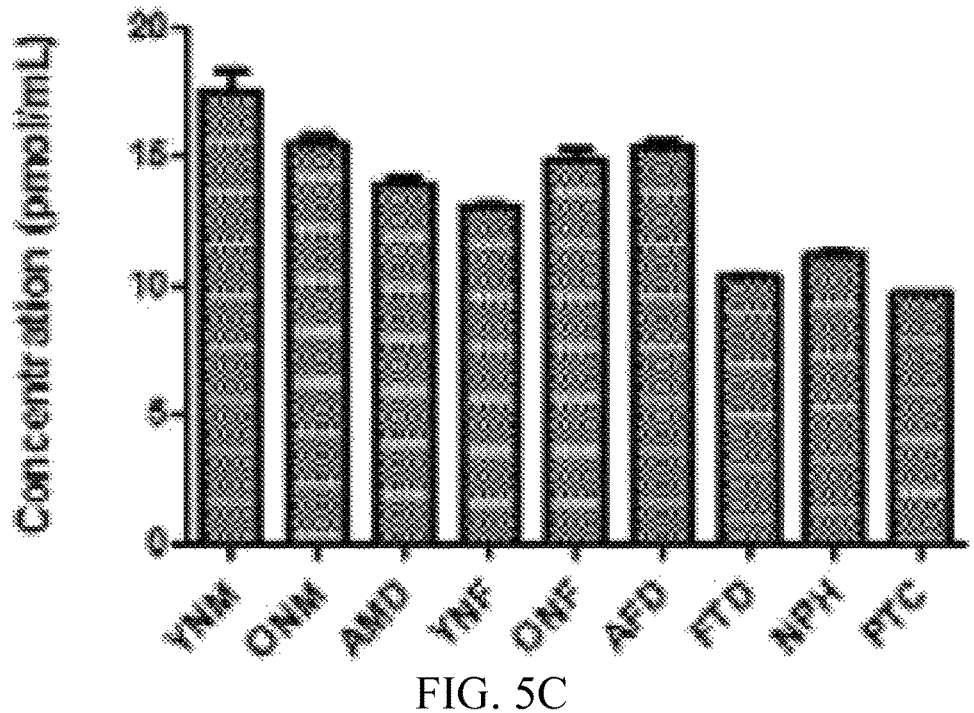
Figure 5D:
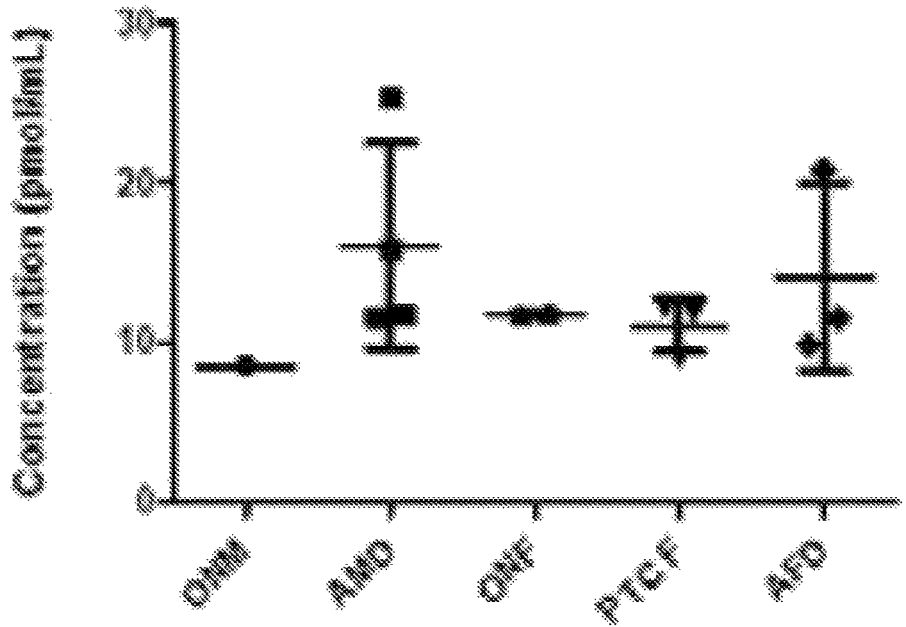
Figures 5E, 5F:
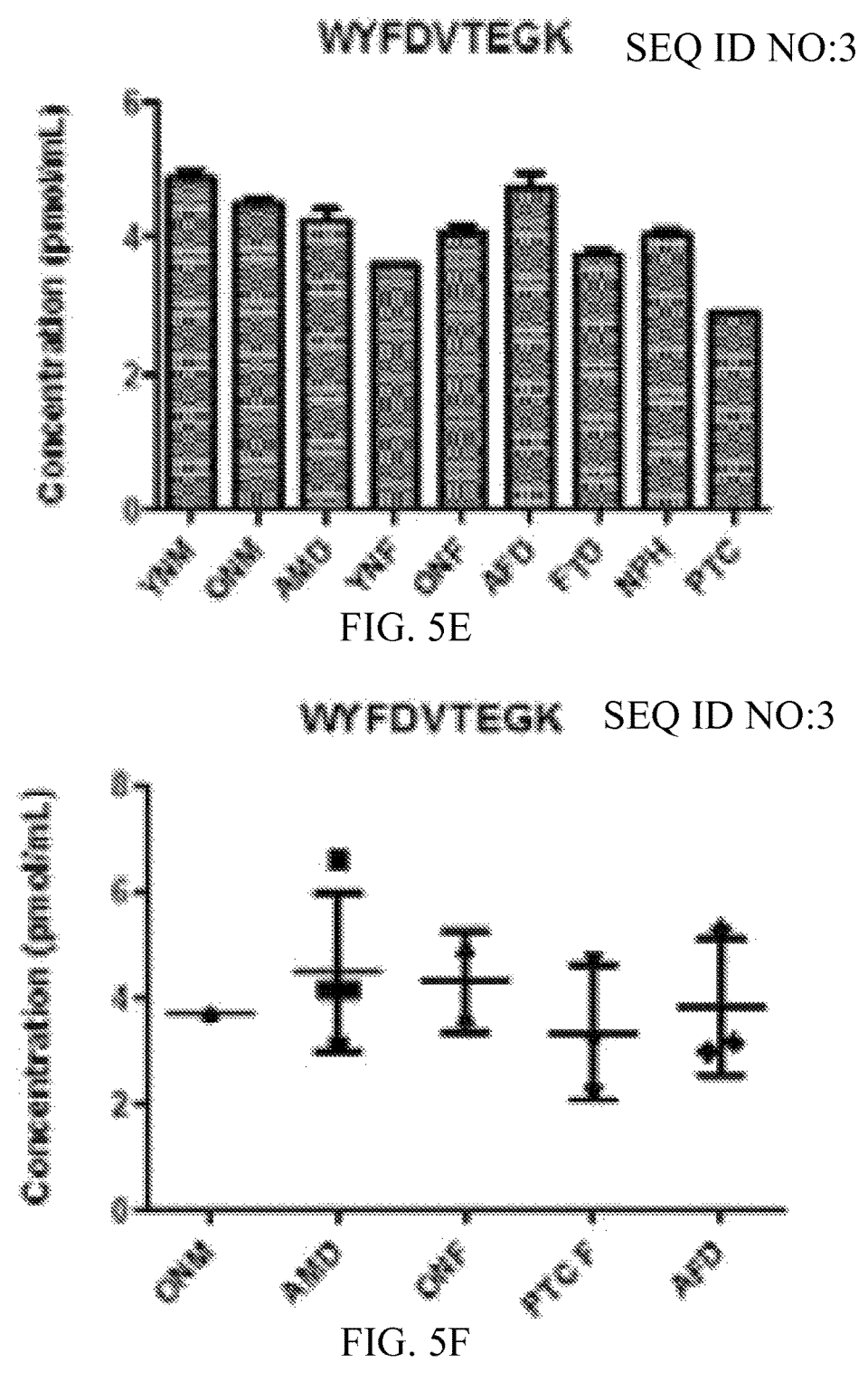
Figure 5G:
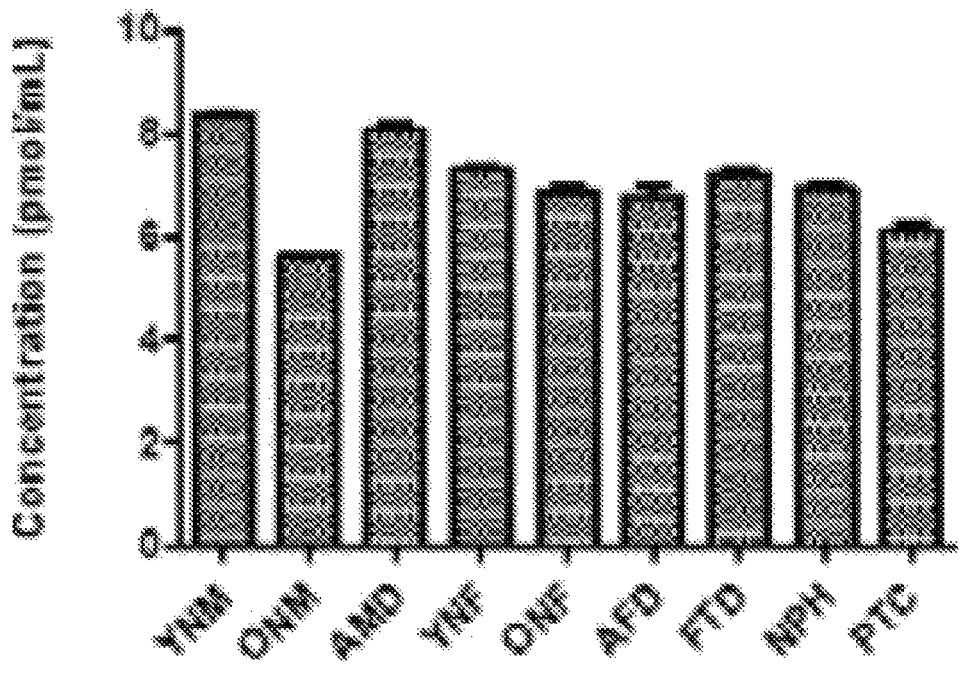
Figure 5H:
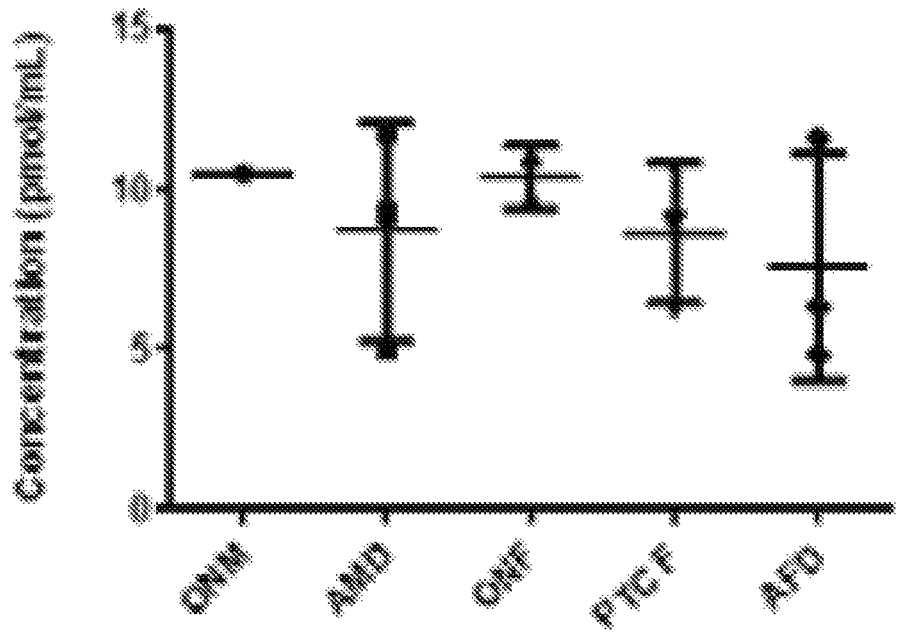
Figure 6A:
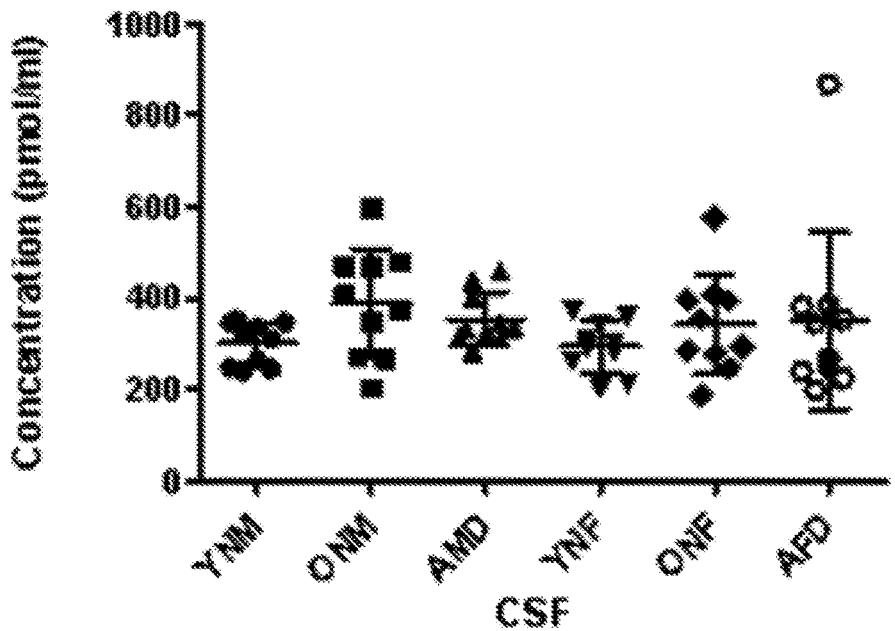
FIGS. 6A-6C. APOE three peptide concentrations in sixty CSF samples.
Figure 6B:
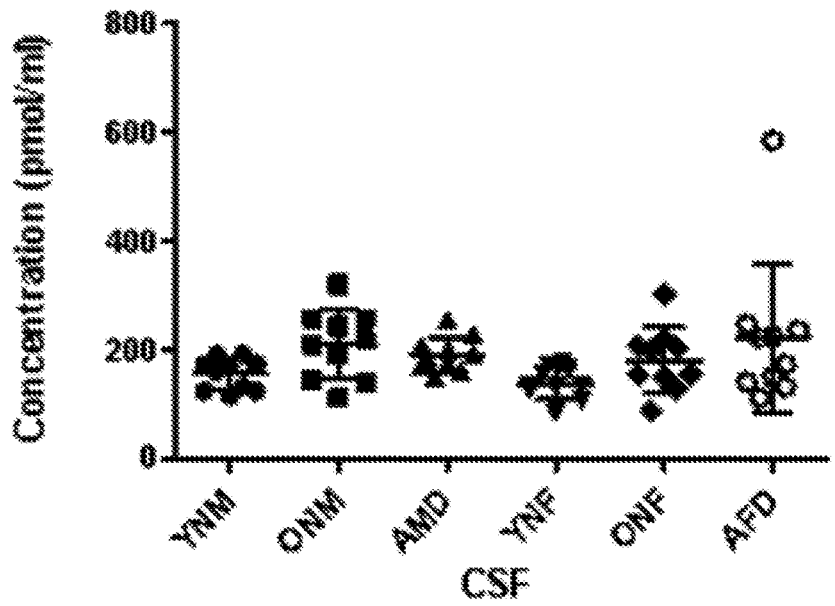
Figure 6C:
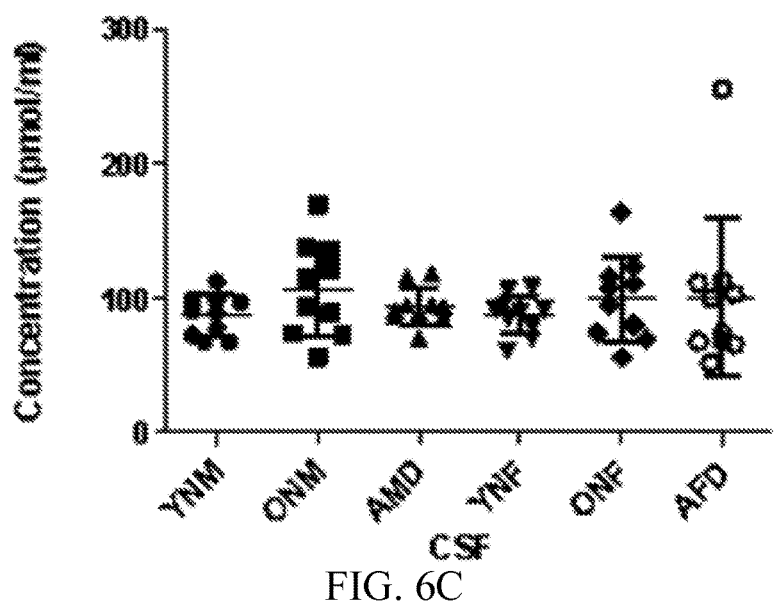
Figure 7A:
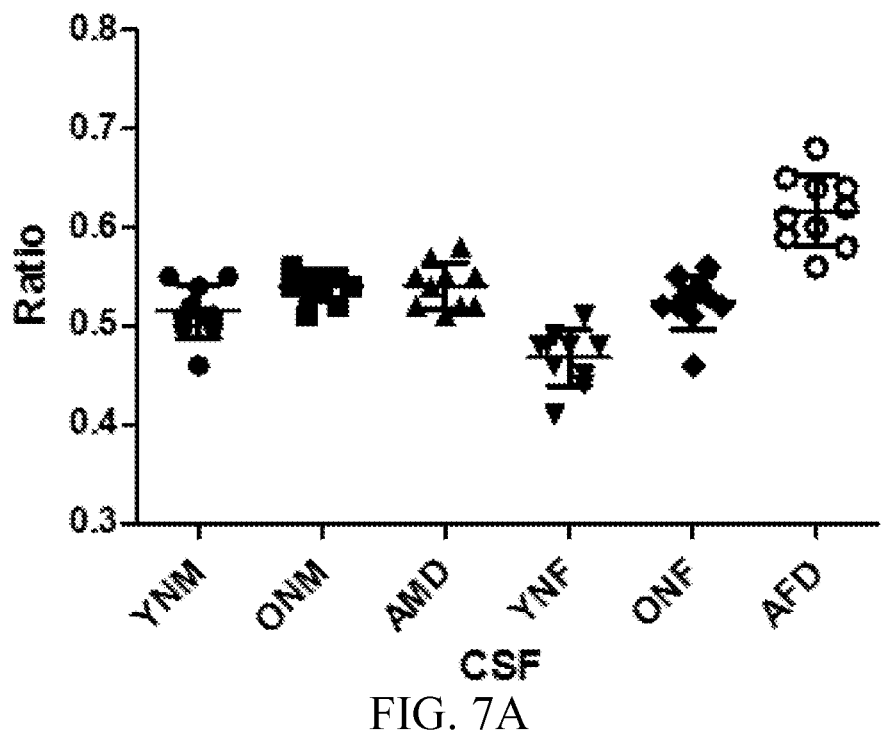
FIGS. 7A-7B. APOE peptide ratio LGP/SEL, AAT/SEL in sixty CSF samples.
Figure 7B:
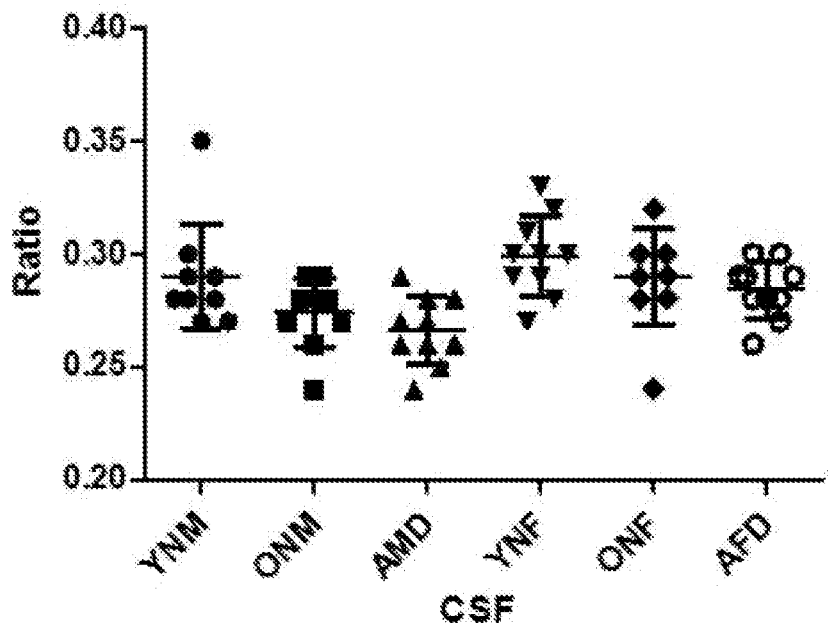
Figure 8A:
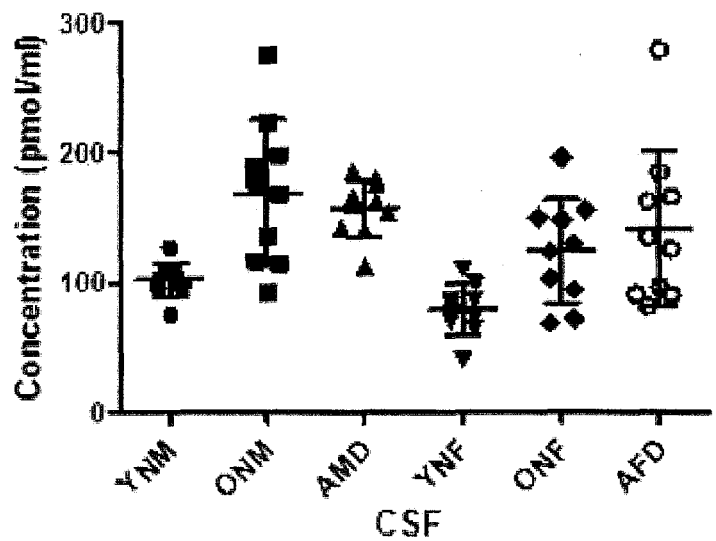
FIGS. 8A-8C. Clusterin three peptide concentrations in sixty CSF samples.
Figure 8B:
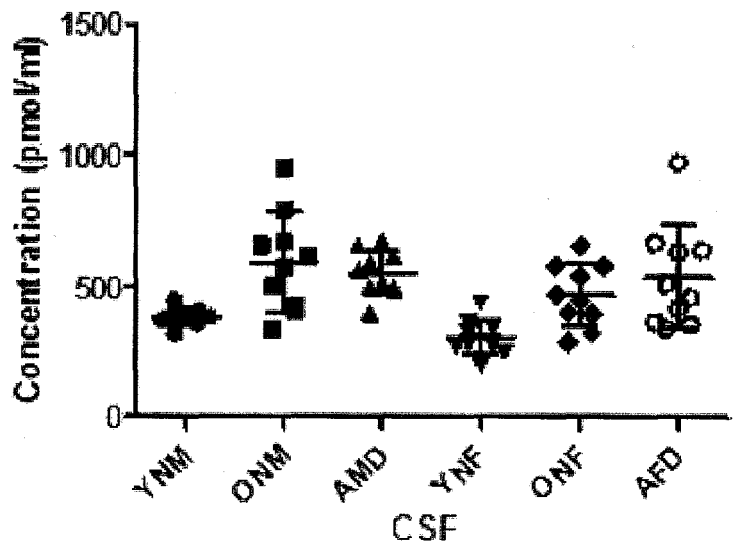
Figure 8C:
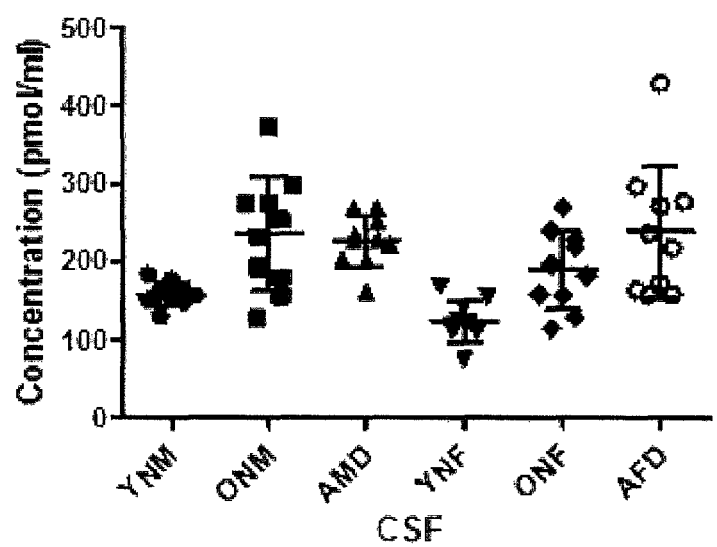
Figure 9A:
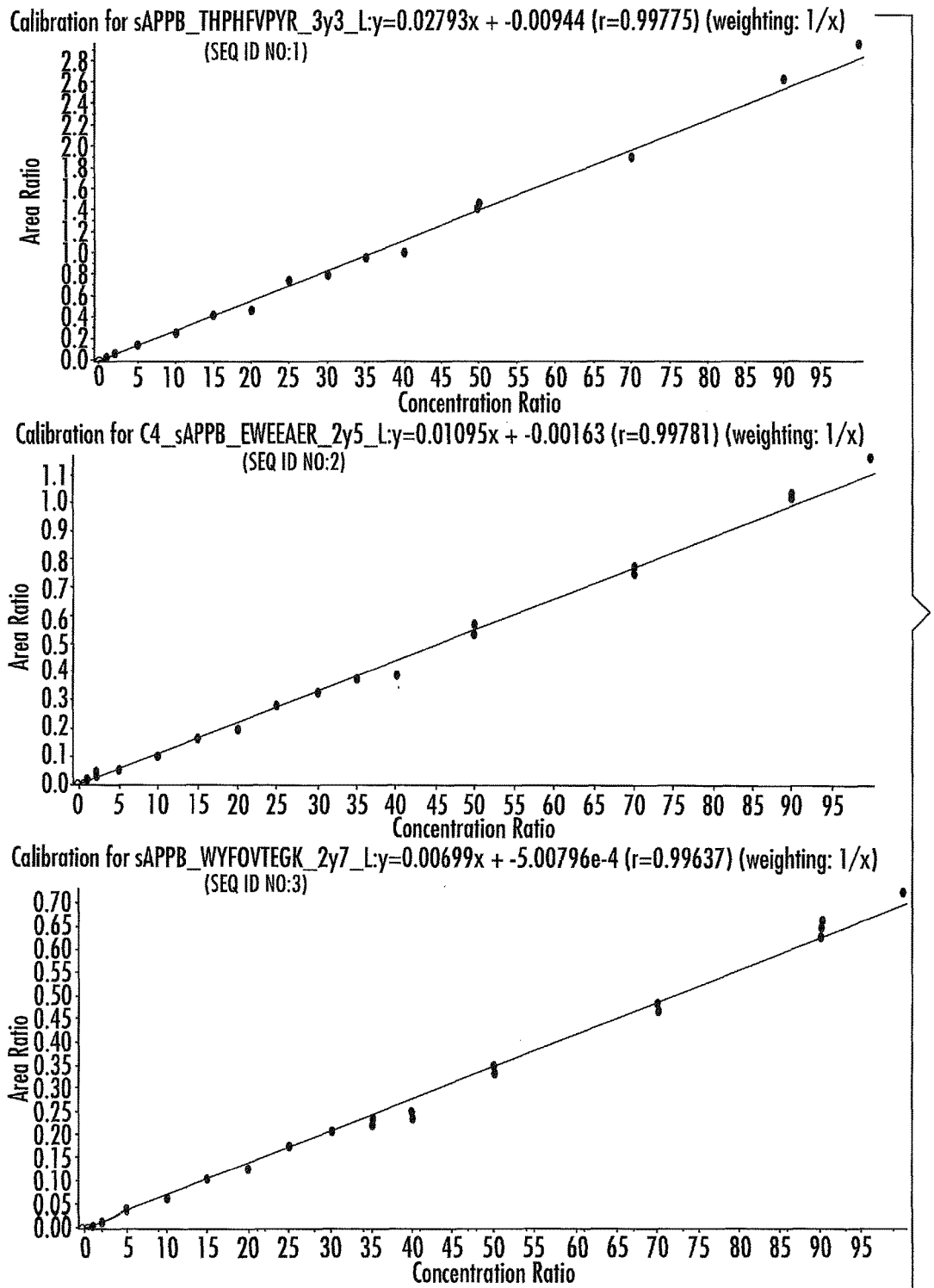
FIG. 9. Calibration curves for APP protein and amyloid beta peptide.
Figure 9B:
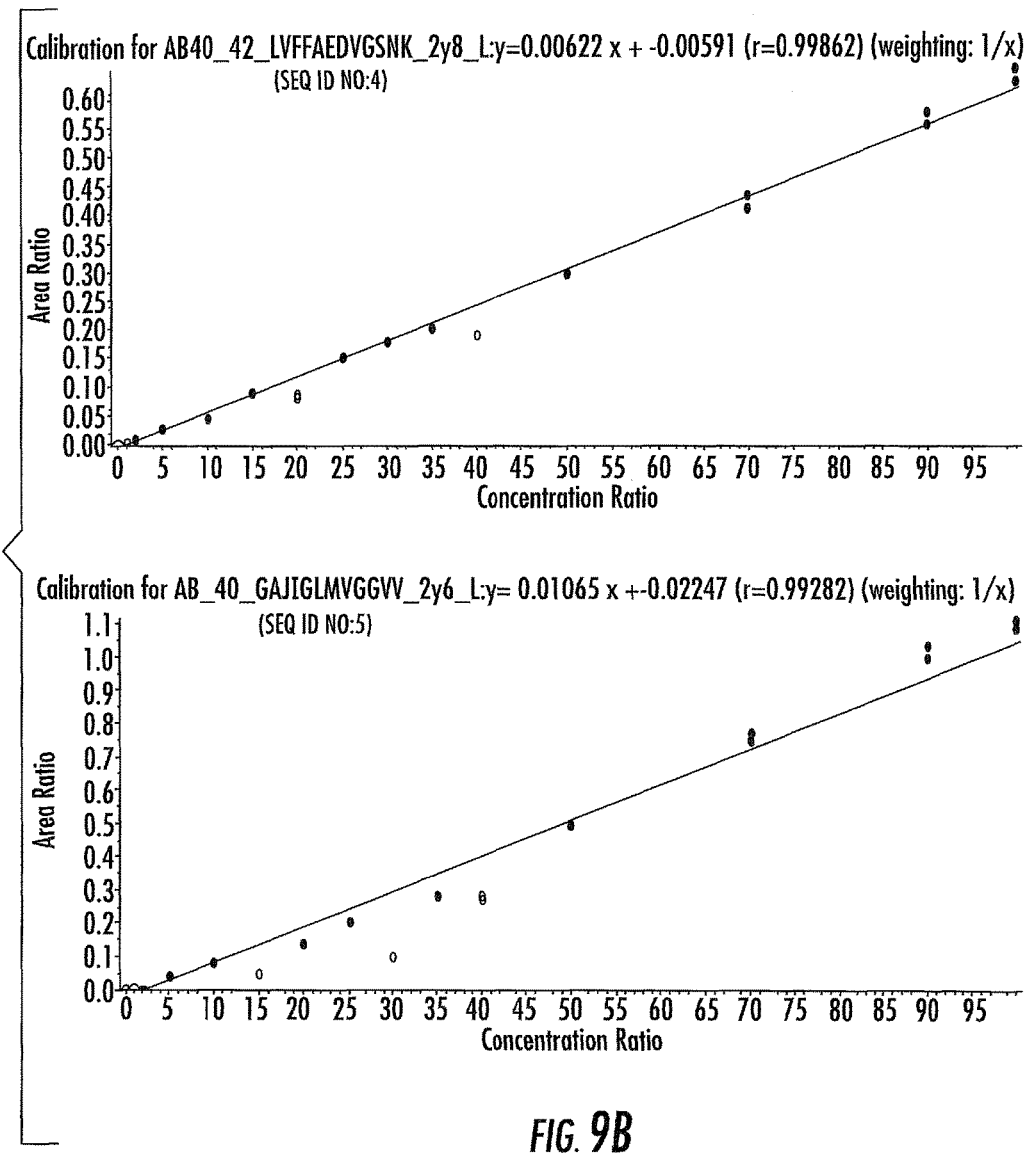
Figure 10:
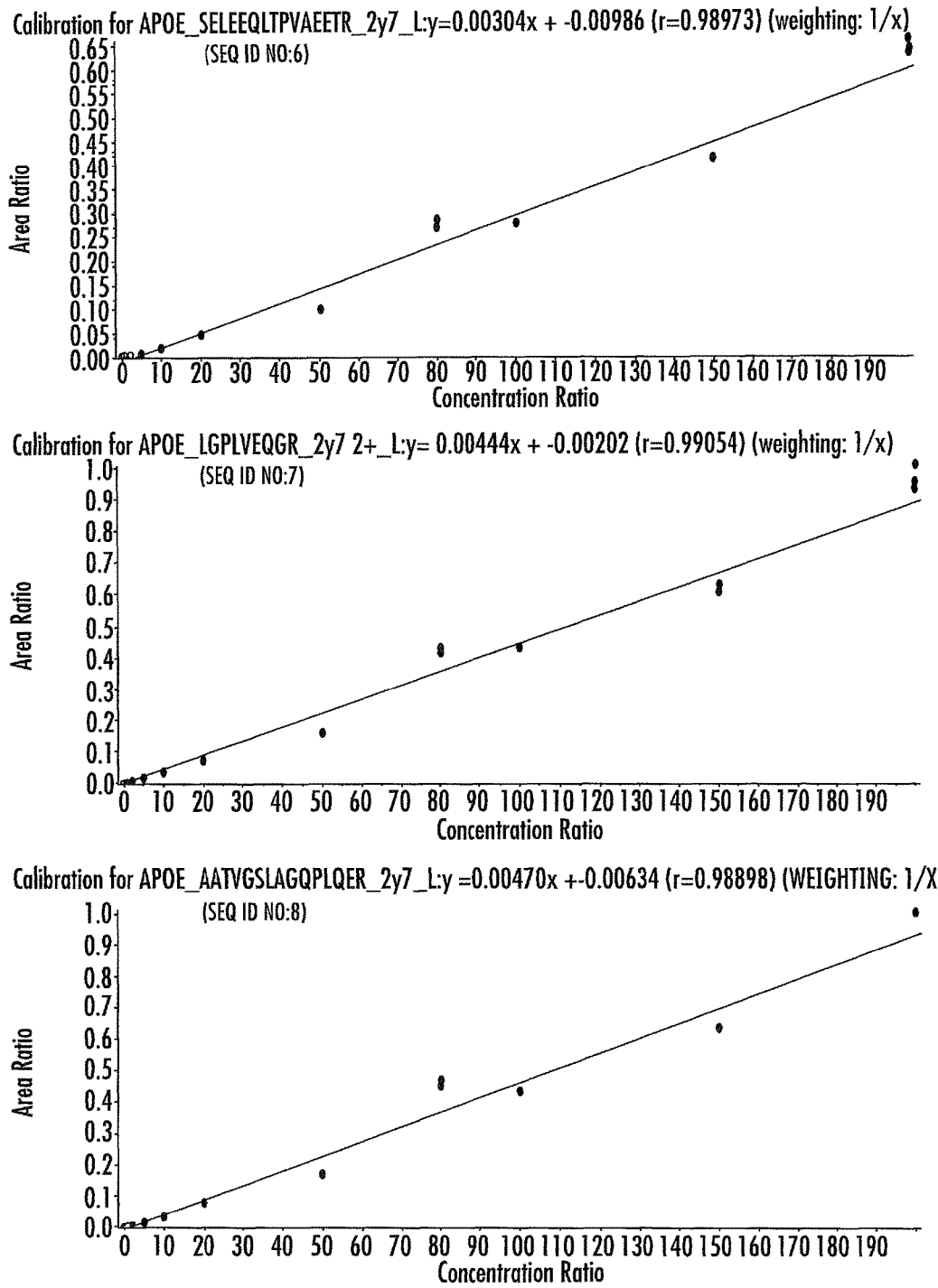
FIG. 10. Calibration curves for APOE protein.
Figure 11:
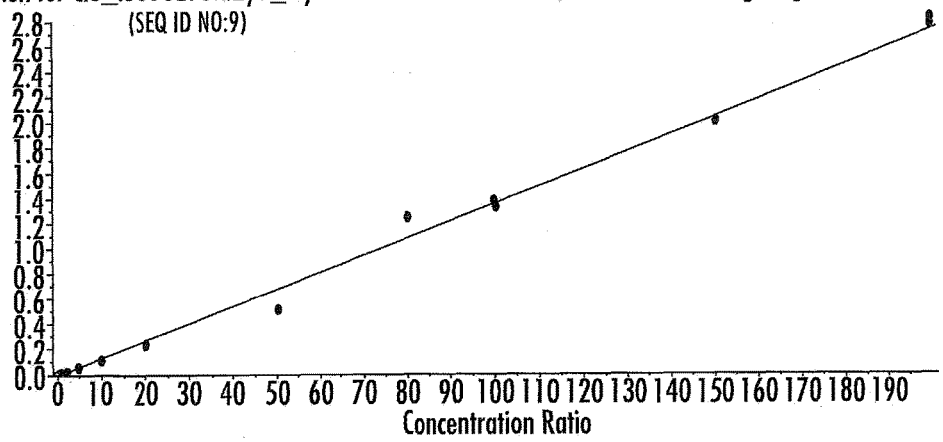
FIG. 11. Calibration curves for Clusterin protein.
Figure 11:
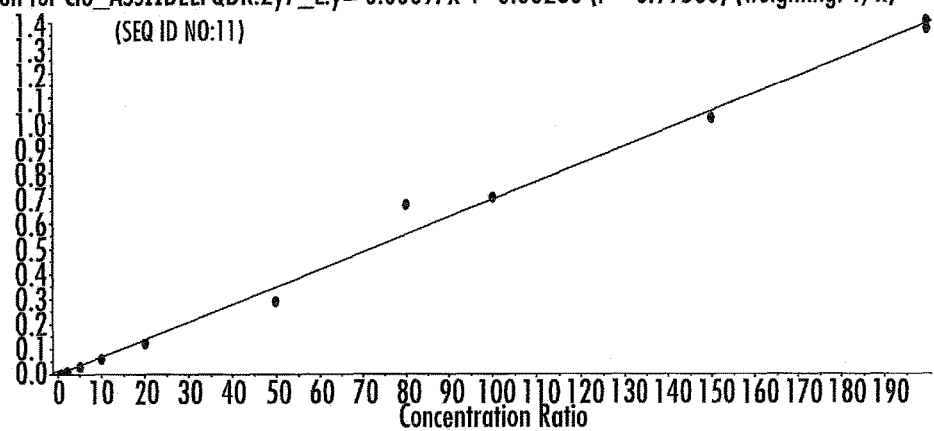
Figure 11:
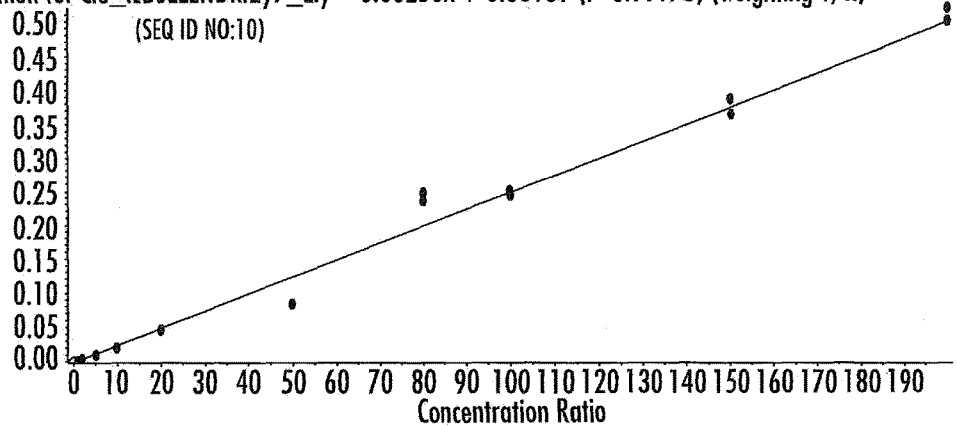
Figure 12:
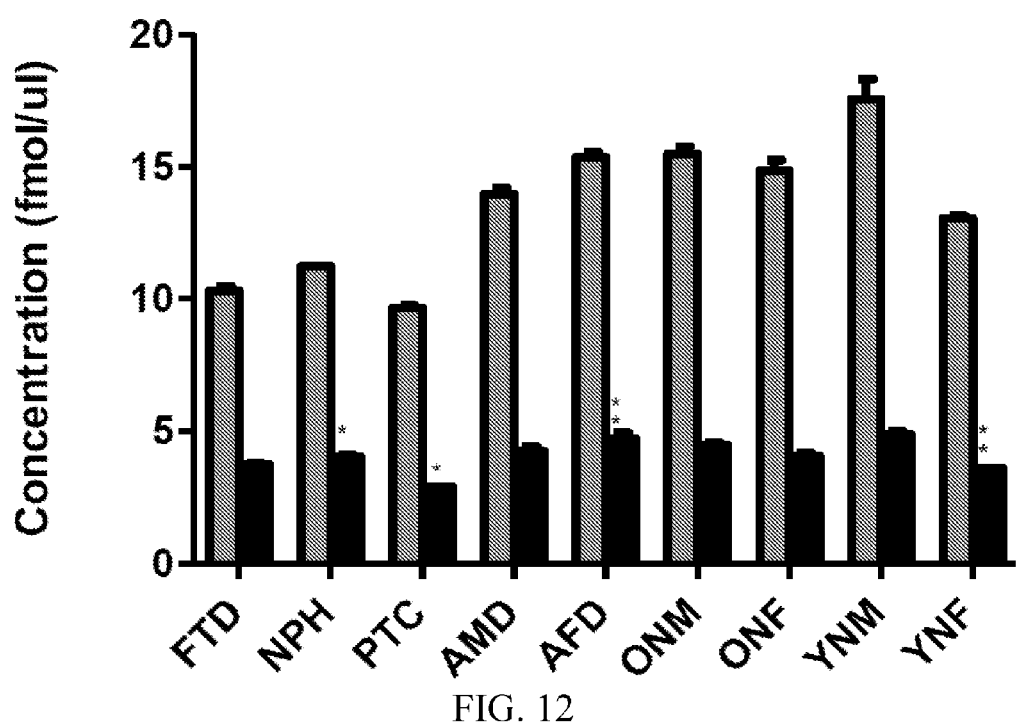
FIG. 12. APP protein concentration (greed) versus two isoforms (APP770 and APP751) concentration, as shown in black, in pooled CSF samples. *P<0.05.
Figure 13:
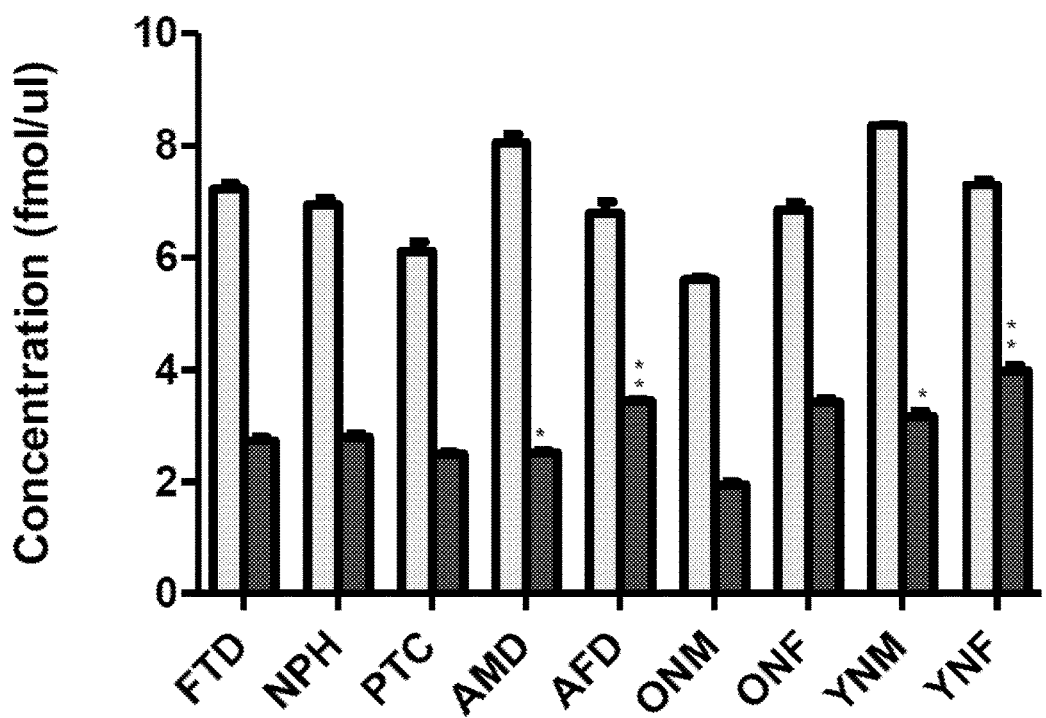
FIG. 13. A beta peptide concentration (yellow) versus a beta 40 peptide concentration, as shown in blue, in pooled CSF samples. *P<0.05.

Chromatogram of heavy peptides was shown in FIG. 5a. Chromatogram of peptides from CSF obtained from a patient with dementia is shown in FIG. 5b.

TABLE 3

Specific peptides in Amyloid precursor protein (APP), Amyloid beta peptide, APOE and Clusterin proteins used for quantification.

| Protein name | Specific peptides | Note |
|---|---|---|
| APP | THPHFVIPYR (SEQ ID NO: 1) | Include all three isoforms (770, 751, 695). |
| | EWEEAER (SEQ ID NO: 2) | Include all three isoforms. |
| | WYFDVTEGK (SEQ ID NO: 3) | Include two of three isoforms (751, 770), missing isoform 695. |
| Amyloid beta | LVFFAEDVGSNK (SEQ ID NO: 4) | Measure all Amyloid beta peptide |
| | GAIIGLMVGGVV (SEQ ID NO: 5) | Specific for Amyloid beta 40 peptide |
| APOE | SELEEQLTPVAEETR (SEQ ID NO: 6) | Measure total APOE |
| | LGPLVEQGR (SEQ ID NO: 7) | Possible cleavage site |
| | AATVGSLAGQPLQER (SEQ ID NO: 8) | Possible cleavage site |
| Clusterin | SGSGLVGR (SEQ ID NO: 9) | |
| | IDSLLENDR (SEQ ID NO: 10) | |
| | ASSIIDELFQDR (SEQ ID NO: 11) | |

TABLE 4

APOE peptide concentrations in CSF samples, mean ± SD (pmol/mL)

| Peptide | YNM | ONM | AMD | YNF | ONF | AFD |
|---|---|---|---|---|---|---|
| SELEEQLTPVAEETR (SEQ ID NO:6) | 299.8 ± 46.2 | 387.2 ± 120.0 | 353.1 ± 59.1 | 293.5 ± 57.0 | 341.6 ± 109.4 | 350.7 ± 193.7 |
| LGPLVEQGR (SEQ ID NO:7) | 155.2 ± 29.5 | 208.4 ± 64.3 | 191.0 ± 31.9 | 138.1 ± 29.1 | 179.8 ± 59.9 | 221.2 ± 136.4 |
| AATVGSLAGQPLQER (SEQ ID NO:8) | 87.1 ± 15.2 | 106.3 ± 35.3 | 93.6 ± 14.0 | 87.4 ± 14.6 | 99.5 ± 31.7 | 101.0 ± 58.4 |

TABLE 5

APOE peptide ratio, mean ± SD.

| Peptide ratio | YNM | ONM | AMD | YNF | ONF | AFD |
|---|---|---|---|---|---|---|
| LGP/SEL | 0.52 ± 0.03 | 0.54 ± 0.01 | 0.54 ± 0.02 | 0.47 ± 0.03 | 0.52 ± 0.03 | 0.62 ± 0.04 ↑ |
| AAT/SEL | 0.29 ± 0.02 | 0.27 ± 0.02 | 0.27 ± 0.02 | 0.30 ± 0.02 | 0.29 ± 0.02 | 0.28 ± 0.01 |

TABLE 6

Clusterin peptide concentrations in sixty CSF samples, mean ± SD (pmol/mL).

| Peptide | YNM | ONM | AMD | YNF | ONF | AFD |
|---|---|---|---|---|---|---|
| SGSGLVGR (SEQ ID NO: 9) | 103.0 ± 13.2 | 169.9 ± 56.3 | 158.1 ± 22.1 | 79.4 ± 19.3 | 124.4 ± 40.2 | 141.4 ± 60.3 |
| IDSLLENDR (SEQ ID NO: 10) | 382.7 ± 34.0 | 592.4 ± 188.0 | 549.4 ± 85.1 | 304.1 ± 67.3 | 466.4 ± 120.4 | 535.5 ± 196.8 |
| ASSIIDELFQDR (SEQ ID NO: 11) | 157.1 ± 15.2 | 234.9 ± 73.8 | 226.1 ± 33.0 | 123.5 ± 26.5 | 188.1 ± 50.0 | 237.3 ± 85.6 |

Conclusions

An integrated SRM assay workflow and target protein quantification method were developed. Specific peptides were selected to measure APP total protein (including three isoforms), APP two isoforms, amyloid beta peptide, amyloid beta 40 peptide, APOE, and Clusterin proteins.

For APP protein and amyloid beta peptide, gender and age are factors affecting protein concentration in cerebrospinal fluid. APP isoform 695 is the predominant form in CSF. APP protein and amyloid beta peptide, amyloid beta 40 peptide decrease in the CSF samples from old people and age matched Alzheimer's disease patients. The measurement of APP and amyloid beta peptide are crucial, and it might serve as therapeutic target for Alzheimer's disease.

Age and gender also play roles in APOE protein concentration in CSF. APOE protein concentration is higher in old people and age matched Alzheimer's disease patients than young people. Two peptides concentrations are lower than one peptide, which means possible cleavage sites in APOE protein. The ratio of two peptides is higher in Alzheimer female patients than the young and old female normal people.

Age and gender affect clusterin concentration in CSF. Clusterin concentration is higher in male than female, also higher in old people than young people.

We claim:

1. A method comprising measuring the levels of total amyloid precursor protein (APP), APP isoform 751, APP isoform 770, amyloid beta 40 peptide, apolipoprotein E (APOE), and Clusterin by performing mass spectrometry with a cerebrospinal fluid sample obtained from a patient.

2. The method of claim 1, wherein the mass spectrometry is multiple reaction monitoring mass spectrometry (MRM-MS).

3. The method of claim 1, wherein performing mass spectrometry comprises adding to the cerebrospinal fluid sample isotopically labeled peptides comprising the amino acid sequence shown in SEQ ID NOS:1-11 to aid in quantitation.

* * * * *

SEQUENCE LISTING

<160> NUMBER OF SEQ ID NOS: 11

<210> SEQ ID NO 1
<211> LENGTH: 10
<212> TYPE: PRT
<213> ORGANISM: Homo sapiens

<400> SEQUENCE: 1

Thr His Pro His Phe Val Ile Pro Tyr Arg
1               5                   10

<210> SEQ ID NO 2

```
<211> LENGTH: 7
<212> TYPE: PRT
<213> ORGANISM: Homo sapiens

<400> SEQUENCE: 2

Glu Trp Glu Glu Ala Glu Arg
1               5

<210> SEQ ID NO 3
<211> LENGTH: 9
<212> TYPE: PRT
<213> ORGANISM: Homo sapiens

<400> SEQUENCE: 3

Trp Tyr Phe Asp Val Thr Glu Gly Lys
1               5

<210> SEQ ID NO 4
<211> LENGTH: 12
<212> TYPE: PRT
<213> ORGANISM: Homo sapiens

<400> SEQUENCE: 4

Leu Val Phe Phe Ala Glu Asp Val Gly Ser Asn Lys
1               5                   10

<210> SEQ ID NO 5
<211> LENGTH: 12
<212> TYPE: PRT
<213> ORGANISM: Homo sapiens

<400> SEQUENCE: 5

Gly Ala Ile Ile Gly Leu Met Val Gly Gly Val Val
1               5                   10

<210> SEQ ID NO 6
<211> LENGTH: 15
<212> TYPE: PRT
<213> ORGANISM: Homo sapiens

<400> SEQUENCE: 6

Ser Glu Leu Glu Glu Gln Leu Thr Pro Val Ala Glu Glu Thr Arg
1               5                   10                  15

<210> SEQ ID NO 7
<211> LENGTH: 9
<212> TYPE: PRT
<213> ORGANISM: Homo sapiens

<400> SEQUENCE: 7

Leu Gly Pro Leu Val Glu Gln Gly Arg
1               5

<210> SEQ ID NO 8
<211> LENGTH: 15
<212> TYPE: PRT
<213> ORGANISM: Homo sapiens

<400> SEQUENCE: 8

Ala Ala Thr Val Gly Ser Leu Ala Gly Gln Pro Leu Gln Glu Arg
1               5                   10                  15

<210> SEQ ID NO 9
<211> LENGTH: 8
<212> TYPE: PRT
```

```
<213> ORGANISM: Homo sapiens

<400> SEQUENCE: 9

Ser Gly Ser Gly Leu Val Gly Arg
1               5

<210> SEQ ID NO 10
<211> LENGTH: 9
<212> TYPE: PRT
<213> ORGANISM: Homo sapiens

<400> SEQUENCE: 10

Ile Asp Ser Leu Leu Glu Asn Asp Arg
1               5

<210> SEQ ID NO 11
<211> LENGTH: 12
<212> TYPE: PRT
<213> ORGANISM: Homo sapiens

<400> SEQUENCE: 11

Ala Ser Ser Ile Ile Asp Glu Leu Phe Gln Asp Arg
1               5                   10
```